United States Patent
Fu et al.

(10) Patent No.: US 9,540,688 B2
(45) Date of Patent: Jan. 10, 2017

(54) REAL-TIME SEQUENCING METHOD FOR SINGLE MOLECULE

(71) Applicant: Personal Genomics, Inc., Grand Cayman (KY)

(72) Inventors: Tsu-Ju Fu, Poway, CA (US); Shang-Chia Chang, Hsinchu County (TW); Jenn-Yeh Fann, Hsinchu County (TW)

(73) Assignee: Personal Genomics, Inc., Grand Cayman (KY)

( * ) Notice: Subject to any disclaimer, the term of this patent is extended or adjusted under 35 U.S.C. 154(b) by 0 days.

(21) Appl. No.: 14/566,715

(22) Filed: Dec. 11, 2014

(65) Prior Publication Data

US 2015/0232928 A1    Aug. 20, 2015

Related U.S. Application Data

(63) Continuation-in-part of application No. 14/183,533, filed on Feb. 19, 2014, now abandoned.

(51) Int. Cl.
C12Q 1/68 (2006.01)
C12P 19/34 (2006.01)

(52) U.S. Cl.
CPC ........... *C12Q 1/6869* (2013.01); *C12Q 1/6876* (2013.01)

(58) Field of Classification Search
CPC .................................................. C12Q 1/6869
USPC ........................................ 435/6.1, 91.1, 91.2
See application file for complete search history.

(56) References Cited

U.S. PATENT DOCUMENTS

| | | | |
|---|---|---|---|
| 3,996,345 | A | 12/1976 | Ullman et al. |
| 4,351,760 | A | 9/1982 | Khanna et al. |
| 5,798,210 | A | 8/1998 | Canard et al. |
| 6,917,726 | B2 | 7/2005 | Levene et al. |
| 7,170,050 | B2 | 1/2007 | Turner et al. |
| 7,486,865 | B2 | 2/2009 | Foquet et al. |
| 7,777,013 | B2 | 8/2010 | Xu et al. |
| 2003/0077610 | A1* | 4/2003 | Nelson et al. ............. 435/6 |
| 2010/0035268 | A1 | 2/2010 | Beechem et al. |
| 2010/0121582 | A1 | 5/2010 | Pan et al. |
| 2011/0076679 | A1 | 3/2011 | Shin et al. |
| 2011/0223590 | A1 | 9/2011 | Chiou et al. |
| 2011/0300534 | A1 | 12/2011 | Chiou et al. |
| 2011/0306039 | A1 | 12/2011 | Chiou et al. |
| 2011/0306143 | A1 | 12/2011 | Chiou et al. |
| 2014/0127680 | A1* | 5/2014 | Emig .............. C12Q 1/6869 435/6.1 |

OTHER PUBLICATIONS

Magde et al, "Thermodynamic Fluctuations in a Reacting System-Measurement by Fluorescence Correlation Spectroscopy," Physical Review Letters, Sep. 11, 1972, pp. 705-708.

Mertz et al., "Single-molecule detection by two-photon-excited fluorescence," Optics Letters, Dec. 15, 1995, pp. 2532-2534.

Barak et al., "Fluorescent Low Density Lipoprotein for Observation of Dynamics of Individual Receptor Complexes on Cultured Human Fibroblasts," The Journal of Cell Biology, Sep. 1981, pp. 595-604.

Medina et al., "Fluorescence correlation spectroscopy for the detection and study of single molecules in Biology," BioEssays, Aug. 2002, pp. 758-764.

Levene et al., "Zero-Mode Waveguides for Single-Molecule Analysis at High Concentrations," Science, Jan. 31, 2003, pp. 682-686.

Venkatesan et al "Nanopore sensors for nucleic acid analysis," Nature Nanotechnology, Oct. 2011, pp. 615-624.

Quail et al., "A tale of three next generation sequencing platforms: comparison of Ion Torrent, Pacific Biosciences and Illumina MiSeq sequencers," BMC Genomics, Jul. 24, 2012, pp. 1-13.

Michael L. Metzker, "Sequencing technologies—the next generation," Nature Reviews Genetics, Jan. 2010, pp. 31-46.

Korlach et al., "Long, Processive Enzymatic DNA Synthesis Using 100% Dye-Labeled Terminal Phosphate-Linked Nucleotides," Nucleosides, Nucleotides and Nucleic Acids, Sep. 2008, pp. 1072-1083.

Korlach et al., "Selective aluminum passivation for targeted immobilization of single DNA polymerase molecules in zero-mode waveguide nanostructures," Proceedings of the National Academy of Sciences, Jan. 29, 2008, pp. 1176-1181.

Eid et al., "Real-Time DNA Sequencing from Single Polymerase Molecules," Science, Jan. 2, 2009, pp. 133-138.

Canard et al., "Catalytic editing properties of DNA polymerases," Proceedings of the National Academy of Sciences, Nov. 1995, pp. 10859-10863.

Guo et al., "Four-color DNA sequencing with 3'-O-modified nucleotide reversible terminators and chemically cleavable fluorescent dideoxynucleotides," Proceedings of the National Academy of Sciences, Jul. 8, 2008, pp. 9145-9150.

Wu et al., "3'-O-modified nucleotides as reversible terminators for pyrosequencing," Proceedings of the National Academy of Sciences, Oct. 16, 2007, pp. 16462-16467.

Kim et al., "Novel 3'-O-Fluorescently Modified Nucleotides for Reversible Termination of DNA Synthesis," ChemBioChem, Jan. 4, 2010, pp. 75-78.

Metzker et al, "Termination of DNA synthesis by novel 3'-modified-deoxyribonucleoside 5'-triphosphates," Nucleic Acids Research, Oct. 11, 1994, pp. 4259-4267.

Seo et al., "Four-color DNA sequencing by synthesis on a chip using photocleavable fluorescent nucleotides," Proceedings of the National Academy of Sciences, Apr. 26, 2005, pp. 5926-5931.

Ruparel et al., "Design and synthesis of a 3'-O-allyl photocleavable fluorescent nucleotide as a reversible terminator for DNA sequencing by synthesis," Proceedings of the National Academy of Sciences, Apr. 26, 2005, pp. 5932-5937.

(Continued)

*Primary Examiner* — Jezia Riley
(74) *Attorney, Agent, or Firm* — Jianq Chyun IP Office

(57) ABSTRACT

This invention is to describe a method for the determination of a nucleic acid sequence, in which it involves an enzyme, an enzyme complex or plural number of enzymes with more than one enzymatic activity and a set of nucleotide analogs, to achieve high signal readout accuracy in nucleic acid sequencing by making each signal to have a long signaling time span which allows a higher signal clarity.

9 Claims, No Drawings

(56) References Cited

OTHER PUBLICATIONS

Turcatti et al., "A new class of cleavable fluorescent nucleotides: synthesis and optimization as reversible terminators for DNA sequencing by synthesis," Nucleic Acids Research, Feb. 7, 2008, pp. e25 1-13.
Canard et al., "DNA polymerase fluorescent substrates with reversible 3'-tags," Gene., Oct. 11, 1994, pp. 1-6.
Welch et al., "Syntheses of Nucleosides Designed for Combinatorial DNA Sequencing," Chemistry—A European Journal, Mar. 1, 1999, pp. 951-960.
Gardner et al., "Determinants of nucleotide sugar recognition in an archaeon DNA polymerase," Nucleic Acids Research, Jun. 1999, pp. 2545-2553.
Willem P. C. Stemmer, "Rapid evolution of a protein in vitro by DNA shuffling," Nature, Aug. 4, 1994, pp. 389-391.
Willem P. C. Stemmer, "DNA shuffling by random fragmentation and reassembly: In vitro recombination for molecular evolution," Proceedings of the National Academy of Sciences, Oct. 1994, pp. 10747-10751.
Crameri et al., "DNA shuffling of a family of genes from diverse species accelerates directed evolution," Nature, Jan. 15, 1998, pp. 288-291.
Kikuchi et al., "Novel family shuffling methods for the in vitro evolution of enzymes," Gene, Aug. 5, 1999, pp. 159-167.
Christians et al., "Directed evolution of thymidine kinase for AZT phosphorylation using DNA family shuffling," Nature Biotechnology, Mar. 1999, pp. 259-264.

O'Maille et al., "Structure-based Combinatorial Protein Engineering (SCOPE)," Journal of Molecular Biology, Aug. 2002, pp. 677-691.
O'Maille et al., "Gene Library Synthesis by Structure-Based Combinatorial Protein Engineering," Methods in Enzymology, Aug. 2004, pp. 75-91.
Coco et al., "DNA shuffling method for generating highly recombined genes and evolved enzymes," Nature Biotechnology, Apr. 2001, pp. 354-359.
Coco et al., "Growth factor engineering by degenerate homoduplex gene family recombination," Nature Biotechnology, Dec. 2002, pp. 1246-1250.
Zhao et al, "Molecular evolution by staggered extension process (StEP) in vitro recombination," Nature Biotechnology, Mar. 1998, pp. 258-261.
Ghadessy et al., "Directed evolution of polymerase function by compartmentalized self-replication," Proceedings of the National Academy of Sciences, Apr. 10, 2001, pp. 4552-4557.
Ong et al., "Directed Evolution of DNA Polymerase, RNA Polymerase and Reverse Transcriptase Activity in a Single Polypeptide," Journal of Molecular Biology, Aug. 18, 2006, pp. 537-550.
Stryer et al., "Fluorescence Energy Transfer as a Spectroscopic Ruler," Annual Review of Biochemistry, Jul. 1978, pp. 819-846.
Cantor et al., "Biophysical Chemistry—part II: Techniques for the Study of Biological Structure and Function," Biochemical Education, Oct. 1981, pp. 157.
Haugland et al., "Dependence of the Kinetics of Singlet-Singlet Energy Transfer on Spectral Overlap," Proceedings of the National Academy of Sciences, May 1969, pp. 23-30.

\* cited by examiner

REAL-TIME SEQUENCING METHOD FOR SINGLE MOLECULE

CROSS-REFERENCE TO RELATED APPLICATION

This application is a continuation-in-part application of and claims the priority benefit of a prior application Ser. No. 14/183,533, filed on Feb. 19, 2014, now pending. The entirety of the above-mentioned patent applications is hereby incorporated by reference herein and made a part of this specification.

BACKGROUND OF THE INVENTION

Field of the Invention

Following the advancements in the detection of single molecules, quite a few measurement methods for single molecules, such as fluorescence correlation spectroscopy (FCS), direct observation using diffraction-limited optics, zero-mode waveguides (ZMW) and nanopore detection, have been developed for various applications. The methodology of single-molecule detection offers much higher sensitivity and provides more detailed information than its conventional bulk measurement counterparts. Optimized systems and methods for single-molecule detection have a great potential for accelerating the DNA sequencing technology. To achieve the single-molecule detection, an optical system can be applied to detect a very weak signal from a selectively excited molecule in a complicated environment. The fundamental elements to a successful detection in this approach rely on clear individual signals and well-defined inter-signal spacing as to generate a collective output of distinct signals.

Understanding the detailed mechanistic processes of DNA polymerization is a basic requirement to design a novel sequencing chemistry. A set of continuous steps are involved in DNA polymerization: First of all, the nucleotide substrates located in the vicinity of primer-template-polymerase complex randomly diffuse to the active site of DNA polymerase and carry out base-pairing trials to the template at the 3'-end of the primer inside the complex. In the following step, any nucleotide should achieve a base-pairing with the DNA template at the DNA polymerase active site, a pyrophosphate is cleaved off from the nucleotide substrate and a phosphodiester bond linkage is formed, catalyzed by DNA polymerase, between the 3'-end of the nascent DNA primer and the 5'-end of this substrate. Then, the last-joined nucleotide becomes the new 3'-end of the primer and the active site of polymerase moves forward to the next position of the template for a new repeating DNA synthesis cycle.

At present, although there are commercially available instruments for optical real-time single molecule sequencing, these sequencing instruments bear high error rates. On possible approach for single molecule sequencing makes use of the fluorescence labeling of the nucleotide, through a connection of a fluorescent dye to the 5'-end polyphosphate of the nucleotide. Different lengths of polyphosphate have been tested and longer versions appear to be preferred for their better performances in the process of sequencing. As described in the proprietary zero-mode-waveguide (ZMW) design, only the fluorescent molecules in a defined volume can be activated and the DNA polymerase is purposely placed within this space. In each compartment of the sequencing cells, it consists DNA polymerase, sequencing template, cognate primer, and all four base-specific fluorescent deoxynucleotide polyphosphates. Since the fluorescent molecules are diffusing in and out freely of the described volume in which the fluorophore activation light can reach, all the activated fluorescent signals of free moving labeled nucleotides within this volume are averaged out to a level of intensity that is considered as background. The current technology has managed to place one DNA polymerase, at most, in each detection compartment. Every nucleotide substrate molecule in the vicinity of DNA-polymerase complex shares the same chance to interact with the complex. If any of those dye-carrying molecules is retained within this area by any reason, its fluorescent signal will become noticeable for detection. In theory, one would be able to detect the fluorescence signal that corresponds to a specific nucleotide substrate when it forms a base pair to the template at the active site of the DNA polymerase. Since the fluorophore is physically connected to the end of a polyphosphate group in each nucleotide substrate, the successful reporting fluorescent signal that corresponds to an adequate base-pairing substrate begins at the moment when this substrate forms a base-pair with the template at the active site (bright phase) and the signal quickly dissipates after the moiety of dye and partial polyphosphate at the 5'-end of nucleotide substrate gets cleaved off from the DNA-polymerase complex and diffuses away. The subsequent event of a phosphodiester bond formation between the monophosphate nucleotide and the nascent primer strand is irrelevant to signal reporting (dark phase). By design, sequencing is achieved via a continuous recording of all incidents for each ephemeral fluorescence flash (bright phase). Since this detection method is very sensitive to the retention time of each fluorescent molecule in the "observing volume", however, some of the unclear lingering of fluorescent molecules can produce false signals and consequently result in generating sequence insertion errors. From the empirical sequencing data collected by the described method, it is important to note that neither every peak in the time-resolved fluorescence intensity spectrum has the same intensity nor the time spans of all signals are identical. Furthermore, the spacing between every two consecutive peaks actually fluctuate quite a lot. A combination of these characteristics is, obviously, posing a serious challenge for any signal-reading algorithm. In real practices, besides the similar problems generated from the impurity of nucleotides, i.e., analog substrates lack fluorophore dyes, deletion errors in sequencing results can also be created by some of the dye-linked phosphates being cleaved off very quickly from their nucleoside moieties so that their fluorescent signals become too transient to be fully picked up. In addition, combining the frequent ambiguous tiny signals with the unpredictable spacing between peaks further worsen the chance of making correct base callings. In order to find an ultimate solution for such matters, fine-tuning the sequence recognition algorithms would not be as efficient as changing the fundamental sequencing chemistry.

BRIEF SUMMARY OF THE INVENTION

This invention describes an approach capable of producing distinct signals so as to allow more accurate readouts for single-molecule real-time DNA sequencing.

DETAILED DESCRIPTION OF THE INVENTION

1. Methods of the Invention 1.1 Overview of the Methods

The rate of DNA replication can be as high as 1,000 bases per second by a DNA polymerase. With the current capability in single molecule detection, the replication speed is at least one to two orders of magnitude higher than what we can do for an accurate base-by-base recording of the DNA synthesis. In order to achieve a valid real-time single molecule sequencing, we have to slow down the rate of DNA replication. Applicants have previously designed a sequencing system that utilizes the exonuclease activities of DNA polymerases to slow down the proceeding of the DNA synthesis. Such system involves a DNA template, a primer, a set of deoxynucleotide analogs with fluorescent tags at their 3'-ends, and a DNA polymerase that is capable of cleaving off the fluorophore moiety of the analog efficiently through its exonuclease activity. The sequencing system can be summarized with the following features: 1) one fluorescent nucleotide analog is added onto the nascent primer in the each step of DNA replication by a DNA polymerase, 2) the replication is stalled temperately due to the 3'-end fluorescent attachment, which could be, for example, an analog of a nucleotide or a dinucleotide, 3) the identity of the added nucleotide is recorded by the fluorescent signal presented in its 3'-end attachment, 4) the 3'-end fluorescent moiety is resolved by the exonuclease activity of the DNA polymerase, and 5) 3'-end hydroxyl group is restored and the last added nucleotide is ready for the next round of nucleotide addition. This Pause-&-Go sequencing design allows us not only to slow down the synthesis speed, but also to make the raw data easier to decipher by intensifying each signal strength (longer signaling time span) and, on some occasions, longer inter-signal spacing. Along the same trend of thought, we have noticed that another route can also be taken in the real time detection of a single molecule sequencing methodology by using the catalytic editing activities in some DNA polymerases or other equivalent enzymatic functions.

The catalytic editing activity of certain DNA polymerases is one of the least studied enzymatic activities of DNA polymerases. A paper indicates that certain DNA polymerases, i.e., Sequenase and HIV reverse transcriptase, are able to incorporate 3'-end esterified nucleotides (with various attachments) into the nascent primer and they also have an esterase-like activity (also called catalytic editing activity or 3' intrinsic editing activity) to cleave off the 3'-end blocking attachments to resume DNA synthesis. From the same report, it is learned that the mentioned activity requires the presence of a correct nucleotide for the next position in primer-template-enzyme complex to carry out the editing function. From this observation, it is supposed that the 3'-modified ends in nucleotides cannot be processed by an esterase activity before participating in DNA synthesis. Although additional experiments may be needed to further confirm the mechanistic details of such hydrolysis reaction, the catalytic editing activity may be useful in cleaving off the 3'-end modification in a modified nucleotide. Herein, it is considered that the catalytic editing activity of some DNA polymerases may also be applied in the real-time single molecule sequencing.

1.2 Nucleotide Analogs

The nucleotides used for real-time single-molecule sequencing has to be carefully chosen to ensure the undisturbed proceeding of the replication during the measurement. From the previous studies, the selected DNA polymerase, i.e., phi 29 DNA polymerase, can utilize a nucleotide substrate with long polyphosphate (up to six phosphates) at the 5'-end. As for those using nucleotides with 3'-end modifications, very limited information is available regarding the DNA polymerase's compatibility with these substrates. As for the replication terminators developed for the Sanger's Sequencing method, quite a few modifications have been made at the 3'-end in order to arrest the DNA amplification permanently or reversibly. The nucleotide analogs compatible with the Pause-&-Go sequencing methodology are listed as follows (Formula I and Formula II):

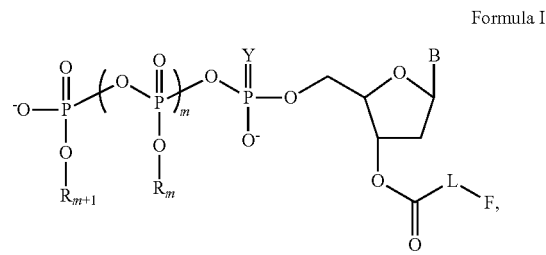

Formula I wherein m is an integer and $1 \leq m \leq 10$, preferably $1 \leq m \leq 7$,
L represents a linker group;
$R_m$ and $R_{m+1}$ vary as m varies, and when m is larger than 1, $R_m$ refers to a set of functional groups ranging from $R_1$ to $R_m$, each of $R_m$ may represent independently hydrogen (H) or a functional group consisting of a linker group $L_m$ and a quencher $Q_m$, while $R_{m+1}$ may represent hydrogen (H) or a functional group consisting of a linker group $L_{m+1}$ and the quencher $Q_{m+1}$, the quencher $Q_m$ or $Q_{m+1}$ is independently chosen and applied to decrease the photo-detectable signal, e.g., fluorescent signal generated from the fluorescent dye, arisen from the label at the 3'-end of the nucleotide; the linker group L, $L_m$ or $L_{m+1}$ is independently selected from alkyl, alkenyl, alkynyl, aryl, heteroaryl, heterocyclyl, polyethylene glycol, ester, amino, sulfonyl, or a combination thereof;
F represents a photo-detectable label;
B represents a base selected from adenine, cytosine, guanine, thymine, uracil, hypoxanthine or 5-methylcytosine; and
Y represents oxygen (O) or sulfur (S), wherein a substitution of O in the phosphate to S is to safeguard the nascent strand from a continuous 3' to 5' hydrolyzation by exonuclease.

Formula II wherein m is an integer and $1 \leq m \leq 10$, preferably $1 \leq m \leq 7$,
L represents a linker group;
$R_m$ and $R_{m+1}$ vary as m varies, and when m is larger than 1, $R_m$ refers to a set of functional groups ranging from $R_1$ to $R_m$, each of $R_m$ may represent independently hydrogen (H) or a functional group consisting of a linker group $L_m$ and a quencher $Q_m$, while $R_{m+1}$ may represent hydrogen (H) or a functional group consisting of a linker group $L_{m+1}$ and the quencher $Q_{m+1}$, the quencher $Q_m$ or $Q_{m+1}$ is independently chosen and applied to decrease the photo-detectable signal, e.g., fluorescent signal generated from the fluorescent dye, arisen from the label at the 3'-end of the nucleotide; the linker group L, $L_m$ or $L_{m+1}$ is independently selected from alkyl, alkenyl, alkynyl, aryl, heteroaryl, heterocyclyl, polyethylene glycol, ester, amino, sulfonyl, or a combination thereof;

F represents a photo-detectable label;

B represents a base selected from adenine, cytosine, guanine, thymine, uracil, hypoxanthine or 5-methylcytosine; and Y represents methyl (—$CH_3$) or boryl (—$BH_2$), wherein a substitution of O in the phosphate to $CH_3$ or $BH_2$ is to safeguard the nascent strand from a continuous 3' to 5' hydrolyzation by exonuclease.

This group of nucleotide substrates will at least transiently arrest the reaction when they are used in DNA synthesis. When such nucleotide substrates are employed in a modified single-molecule real-time sequencing system, the fluorescent signal lights up right after the substrate is base-paired with the template at the active site of a DNA polymerase and lasts until the dye moiety is cleaved away from the DNA-polymerase complex by the catalytic editing activity of DNA polymerase. In a similar approach, the dye-cleavage process may also be carried out by another enzyme or an enzyme moiety that is linked to a DNA polymerase. The sequencing process of the 3'-dye substrates involve at least two enzymatic activities, i.e., polymerization and catalytic editing activities, to complete each nucleotide addition cycle. Compared to the sequencing scheme using 5'-end dye-labeled (5'-dye) substrates, the prolonged signals generated from the above described 3'-end dye-labeled (3'-dye) nucleotide substrates are more accurate. For the polymerization at the 5'-end and the catalytic editing at the 3'-end of the same nucleotide, it is unclear whether these two activities are actually correlated. Two interesting observations have been reported on this matter: 1) the pre-incubation of 3'-esterified analogues with Sequenase in the absence of DNA primer/template doesn't make the treated analogues become replication-ready substrates for Taq polymerase in a regular primer extension reaction, 2) the appearance of the correct nucleotide for the next position in a stalled primer extension reaction is a prerequisite of the catalytic editing activity. These evidences suggest that the 3' esterase and the polymerase active sites may be the same or at least be near one another and work closely together. Using the molecular base-pairing event between a correct analogue and the template at the polymerase active site as a marking point, the fluorescent label of a 5'-dye analogue is cleaved off at the time very close to the marking point but the counterpart reaction of the 3'-dye analogue may not occur until the next base-pairing takes place. In another word, the fluorescent signal in both cases begins at the moment when the substrate approaching the active site for base-pairing and this signal ends at the formation of phosphodiester bond of the same round of base-pairing for the 5'-dye substrate, but it ends only slightly before or around the next round of base-paring event for the 3'-dye substrate. The sequencing signal produced from the 3'-dye nucleotide lasts longer and is more distinguishable from the background; that is, the signal recognition algorithm can filter out the false signals generated from the transient lingering of non-specific labeled molecules with less efforts. In this design, the fluorophore attachment at the 3'-end of the nucleotide not only serves as a signal reporter but also functions as a staller in the polymerization. Only when the 3'-end blockage group is eventually removed by an enzymatic catalytic editing activity, the DNA synthesis resumes. Overall, the DNA synthesis is in a Pause-&-Go mode for every single nucleotide addition.

The time at which the catalytic activity occurs remains to be determined. If the 3'-end labeling group is cleaved after the next modified nucleotide base-pairing to the target at the active site of a DNA polymerase, interferences may occur in the overall signal outputs between the two fluorophores in close vicinity at this location. Although the total signal display of such event will be largely dependent on the mechanistic nature of such enzymatic reaction and the choice of fluorophore sets, the underlying disciplines of the detection described here remain unchanged.

In a sequencing system, it may comprise a target nucleic acid, a primer nucleic acid comprising a sequence which is complementary to a region of the target nucleic acid, a nucleic acid-polymerizing enzyme, a reaction buffer which contains acceptable salts, and a set of photo-detectable nucleotide analogs. One of the most critical characteristic of this method is to use a set of base-specific photo-detectable labels (e.g., fluorescent labels, attached to 3'-ends of the nucleotides that can be enzymatically cleaved from the nucleotides during replication). Using this design, the DNA polymerase, the enzyme complex, or the enzyme mixture that possesses a 5' to 3' polymerization activity and a 3'-end catalytic editing activity is required to work with the 3'-end modified nucleotides to ensure the replication process not to be interrupted or stopped. Each of those nucleotide analogs has a base moiety capable of base-pairing with the template and at least one photo-detectable label specifically bonded to the base moiety. One important aspect of the analog is that the photo-detectable label is linked to the 3' position of the sugar of the nucleotide through a coupler and a linker. The coupler is an enzyme resolvable segment, and the linker connects the photo-detectable label to the nucleotide through the coupler. The linker mainly functions to fine-tune the steric interaction between the nucleotide and the photo-detectable label so that the analog can fit better into the activity center of the DNA polymerase. The main criterion of these analogs is to serve as good substrates for the DNA polymerase in DNA polymerization. On the other hand, in order to efficiently utilizing these analogs, the DNA polymerase may be functionally optimized by the protein engineering methodology, e.g., in vitro evolution (directed evolution). Different colors of fluorescent labels may be used in a base-specific fashion among the analogs. When one of these custom designed analogs is incorporated into the nascent strain of DNA during DNA polymerization (or primer extension), the photo-detectable label that is physically connected to the nucleotide can be activated, e.g., by UV radiation, and the identity of the analog involved in the latest round of nucleotide addition is revealed. A further cleavage of the photo-label is carried out so that the nascent DNA strand is no longer blocked at its 3'-end and available for replication and the nascent DNA can be further extended. The labeling of cleavable fluorophores may be used on either the 3'- or the 5'-end of their nucleotide analogs, for example, descriptions in U.S. Pat. No. 5,798,210 and U.S. Pat. No. 8,354,252. Herein, the described method of this invention allows the uninterrupted and continuous observation for reading the identity of each nucleotide being added on the nascent strand DNA during the replication process in real time.

The steric hindrance is the main concern for the reaction between the enzyme and the substrate (the substrate analog). Each of the nucleotide analogs disclosed herein has two parts: a nucleotide and a fluorophore. In order to fit the analog better into the activity center of the DNA polymerase, a linker connecting the nucleotide and the fluorophore may play a critical role. In order to select the proper nucleotide analogs for sequencing reactions, different lengths of phosphate groups between the nucleotide and its fluorophore have been studied. Among the various commercial fluorophore-labeled nucleotide analogs used for DNA labeling, different lengths of alkane, alkene, alkyne, or a combination of them have been used as linkers between the nucleotide and the fluorophore moiety. It is learned that linkers of the nucleotide analogs are useful tools to optimize the efficiency of their participation in DNA replications.

Other than linkers, the couplers that connect the linker and the nucleotide also have to be considered in the analog design. Herein, the photo-detectable label and the linker may be considered as a label moiety connected to the nucleotide via the coupler in the nucleotide analog. Since the label moiety attached at the 3'-end of the nucleotide analog could block the addition of the next nucleotide, it is important to make the 3'-end accessible between any two consecutive nucleotide additions. The sequencing method of this invention exploits an enzymatic activity or a combination of enzymatic activities, instead of involving non-continuous chemical treatments, to achieve a real-time observation of each nucleotide addition to the nascent strand. The couplers of choice have to be cleavable by an enzyme or a mixture of enzymes so that the fluorophore moiety is cut off to present the extendable DNA 3'-end and sequencing process can be carried out continuously. As long as the coupler is cleavable by the enzyme used in the sequencing process, the coupler should not be limited to a specific type of functional groups. Taking advantage of the catalytic editing activity of the DNA polymerase, the ester group (—O—(CO)—) may be used as the coupler as the ester group is cleavable by the DNA polymerase and no additional enzyme is required.

Other possible candidates for the coupler groups may be selected from —O—, —S—, —HN—, —$PO_4^-$—, —COO—, —CO—, —NH(CS)NH—, or —NHCO—, depending on the enzyme(s) used in the sequencing reaction. Exemplary nucleotide analog has a structure as shown in Formula IA or Formula IIA:

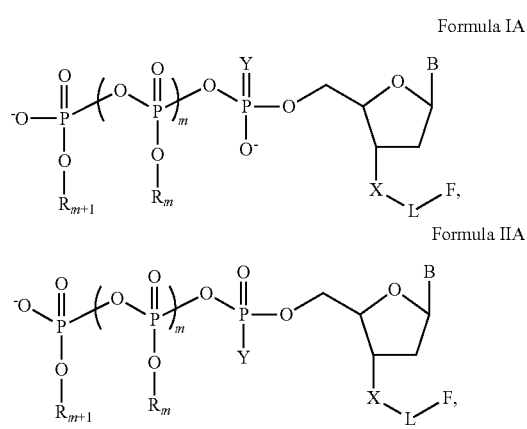

Formula IA

Formula IIA wherein m is an integer and 1≤m≤10, L represents a linker group;

$R_m$ and $R_{m+1}$ vary as m varies, and when m is larger than 1, $R_m$ refers to a set of functional groups ranging from $R_1$ to $R_m$, each of $R_m$ may represent independently hydrogen (H) or a functional group consisting of a linker group $L_m$ and a quencher $Q_m$, while $R_{m+1}$ may represent hydrogen (H) or a functional group consisting of a linker group $L_{m+1}$ and the quencher $Q_{m+1}$, the quencher $Q_m$ or $Q_{m+1}$ is independently chosen and applied to decrease the photo-detectable signal, e.g., fluorescent signal generated from the fluorescent dye, arisen from the label at the 3'-end of the nucleotide; the linker group L, $L_m$ or $L_{m+1}$ is independently selected from alkyl, alkenyl, alkynyl, aryl, heteroaryl, heterocyclyl, polyethylene glycol, ester, amino, sulfonyl, or a combination thereof;

X represents a coupler group selected from —O—, —S—, —HN—, —$PO_4^-$—, —COO—, —CO—, —NH(CS)NH—, or —NHCO—;

F represents a photo-detectable label;

B represents a base selected from adenine, cytosine, guanine, thymine, uracil, hypoxanthine or 5-methylcytosine; and Y in Formula IA represents oxygen (O) or sulfur (S), while Y in Formula IIA represents methyl (—$CH_3$) or boryl (—$BH_2$).

1.2.1 Nucleotide Analog Details

As shown in Formula I & II, the base B may be, for example, a purine or a pyrimidine. For example, the base B may be an adenine, cytosine, guanine, thymine, uracil, or hypoxanthine. The base B may also be, for example, a naturally-occurring or a synthetic derivative of a base, including pyrazolo(3,4-d)-pyrimidine; 5-methylcytosine (5-me-C); 5-hydroxymethyl cytosine; xanthine; hypoxanthine; 2-aminoadenine; 6-methyl or other alkyl derivatives of adenine or guanine; 2-propyl or other alkyl derivatives of adenine or guanine; 2-thiouracil; 2-thiothymine; 2-thiocytosine; 5-propynyl uracil; 5-propynyl cytosine; 6-azo uracil; 6-azo cytosine; 6-azo thymine; pseudouracil; 4-thiouracil; 8-halo (e.g., 8-bromo), 8-amino, 8-thiol, 8-thioalkyl, 8-hydroxyl and other 8-substituted adenine or guanine; 5-halo (e.g., 5-bromo), 5-trifluoromethyl and other 5-substituted uracil or cytosine; 7-methylguanine; 7-methyladenine; 8-azaguanine; 8-azaadenine; deazaguanine; 7-deazaguanine; 3-deazaguanine; deazaadenine; 7-deazaadenine; 3-deazaadenine; pyrazolo(3,4-d)pyrimidine; an imidazo(1, 5-a)-1,3,5 triazinone; a 9-deazapurine; an imidazo(4,5-d)-pyrazine; a thiazolo(4,5-d)-pyrimidine; a pyrazin-2-one; a 1,2,4-triazine; a pyridazine; a 1,3,5 triazine; or the like.

In some embodiments, the moiety L, $L_m$ and $L_{m+1}$ are linkers. Suitable linkers include, for example, alkyl, alkenyl, alkynyl, aryl, heteroaryl, heterocyclyl, polyethylene glycol, ester, amino, sulfonyl, or the combinations of them. The linker may be any suitable functional group which is non-reactive and minimizes steric hindrance between the photo-detectable label and the remainder of the nucleotide analog.

The photo-detectable label F may be any moiety that can be attached to or associated with a nucleotide analog and functions to provide a detectable signal. In some embodiments, the photo-detectable label is a fluorescent compound, such as a small molecule fluorescent label. Useful fluorescent molecules (fluorophores) suitable as a fluorescent label include, but are not limited to: 1,5 IAEDANS; 1,8-ANS; 4-methylumbelliferone; 5-carboxy-2,7-dichlorofluorescein; 5-carboxyfluorescein (5-FAM); fluorescein amidite (FAM); 5-carboxynapthofluorescein; tetrachloro-6-carboxyfluorescein (TET); hexachloro-6-carboxyfluorescein (HEX); 2,7-dimethoxy-4,5-dichloro-6-carboxyfluorescein (JOE); VIC®; NED™; tetramethylrhodamine (TMR); 5-carboxytetramethylrhodamine (5-TAMRA); 5-HAT (Hydroxy Tryptamine); 5-hydroxy tryptamine (HAT); 5-ROX (carboxy-X-rhodamine); 6-carboxyrhodamine 6G; 6-JOE; Light Cycler® red 610; Light Cycler® red 640; Light Cycler® red 670; Light Cycler® red 705; 7-amino-4-methylcoumarin; 7-aminoactinomycin D (7-AAD); 7-hydroxy-4-methylcoumarin; 9-amino-6-chloro-2-methoxyacridine; 6-methoxy-N-(4-aminoalkyl)quinolinium bromide hydrochloride (ABQ); Acid Fuchsin; ACMA (9-amino-6-chloro-2-methoxyacridine); Acridine Orange; Acridine Red; Acridine Yellow; Acriflavin; Acriflavin Feulgen SITSA; AFPs-AutoFluorescent Protein-(Quantum Biotechnologies); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamine-IsoThioCyanate); True Blue; TruRed; Ultralite; Uranine B; Uvitex SFC; WW 781; X-Rhodamine; X-Rhodamine-5-(and -6)-Isothiocyanate (5(6)-XRITC); Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor® dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), also covering a wide spectrum such as Cy3, Cy3B, Cy3.5, Cy5, Cy5.5, Cy7; members of the Oyster® dye fluorophores (Denovo Biolabels) such as Oyster-500, -550, -556, 645, 650, 656; members of the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor® series or Quasar® series of dyes (Biosearch Technologies) such as CAL Fluor® Gold 540, CAL Fluor® Orange 560, Quasar® 570, CAL Fluor® Red 590, CAL Fluor® Red 610, CAL Fluor Red 635, Quasar® 570, and Quasar® 670.

In some embodiments, the photo-detectable label F interacts with a second photo-detectable moiety to modify the detectable signal provided by the first or second label, e.g., via Fluorescence resonance energy transfer ("FRET"; also known as Förster resonance energy transfer). In some embodiments, nucleotides incorporated into a nascent strand are detected using fluorescence resonance energy transfer (FRET)-based detection. For example, in some embodiments, a FRET-based method as described in U.S. Patent Application No. 2010/0035268 can be used. In such embodiments, a Quantum dot capable of acting as a fluorescence donor may be linked to a sequencing primer, and the nucleotide analogs used to synthesize the growing strand carry a label F which is a fluorescence acceptor. Incorporation of the fluorophore-labeled nucleotide analog into the growing nucleotide strand at a nucleic acid polymerizing enzyme active site is detected in real-time by detecting emission of the analog-linked fluorescence acceptor following fluorescence resonance energy transfer from the excited Quantum dot fluorescence donor. The identity of each incorporated nucleotide analog is determined by its fluorescent label, which is detectable while the analog is incorporated into the growing strand and until the attached moiety of the analog comprising the fluorescent label is removed by the catalytic editing activity of the polymerase.

In some embodiments, the nucleotide analog comprises a fluorescence quenching group (quencher) Q. A fluorescence quenching group includes any moiety that is capable of absorbing the energy of an excited fluorescent label when located in close proximity to the fluorescent label and capable of dissipating that energy without the emission of visible light. Suitable fluorescence quenching groups include, for example, Deep Dark Quencher I (DDQ-I); 4-((4-(dimethylamino)phenyl)azo)benzoic acid, succinimidyl ester (DABCYL); Eclipse® dark quencher; Iowa Black® FQ; BHQ-1; QSY-7; BHQ-2; Deep Dark Quencher II (DDQ-II); Iowa Black® RQ; QSY-21; BHQ-3, and the like. A fluorescence quenching group Q may be linked to the gamma or beta phosphate of a nucleotide analog. A fluorescence quenching group may be connected via a linker $L_x$ to the gamma or beta phosphate of the nucleotide triphosphate analog, or any of the phosphate groups after the gamma position. Suitable linkers include, for example, alkyl, alkenyl, alkynyl, aryl, heteroaryl, heterocycloalkyl, polyethylene glycol, ester, amino, sulfonyl linkers, or the like and a combination of them. The linker may be any suitable linker which is nonreactive and which minimizes steric hindrance between the fluorescence quenching group and the remainder of the nucleotide analog.

The term "alkyl" as used herein refers to a saturated straight or branched hydrocarbon functional group, such as a straight or branched alkyl group of 1-22, 1-8, or 1-6 carbon atoms, referred to herein as $C_1$-$C_{22}$ alkyl, $C_1$-$C_8$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkenyl" as used herein refers to an unsaturated straight or branched hydrocarbon functional group having at least one carbon-carbon double bond, such as a straight or branched alkenyl group of 2-22, 2-8, or 2-6 carbon atoms, referred to herein as $C_2$-$C_{22}$ alkenyl, $C_2$-$C_8$ alkenyl, and $C_2$-$C_6$ alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkynyl" as used herein refers to an unsaturated straight or branched hydrocarbon functional group having at least one carbon-carbon triple bond, such as a straight or branched group of 2-22, 2-8, or 2-6 carbon atoms, referred to herein as $C_2$-$C_{22}$ alkynyl, $C_2$-$C_8$ alkynyl, and $C_2$-$C_6$ alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$C_6$ aryl."

The term "heteroaryl" as used herein refers to a mono-, bi-, or multi-cyclic, aromatic ring system containing one or more heteroatoms, for example one to three heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "($C_2$-$C_5$)heteroaryl."

The term "heterocyclyl" or "heterocycle" as used herein refer to a saturated or unsaturated 3-, 4-, 5-, 6- or 7-membered ring system containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl-, —C(O)—O-alkyl-, -alkyl-C(O)—O-alkyl-, etc. Exemplary esters also include aryl or heteroaryl esters, e.g. wherein at least one of $R_j$ or $R_k$ is a heteroaryl group such as pyridine, pyridazine, pyrmidine and pyrazine, such as a nicotinate ester. Exemplary esters also include reverse esters having the structure —$R_k$C(O)O—, where the oxygen is bound to the parent molecular group. Exemplary reverse esters include succinate, D-argininate, L-argininate, L-lysinate and D-lysinate. Esters also include carboxylic acid anhydrides and acid halides.

The term "amino" as used herein refers to the form —$NR_dR_e$ or —$N(R_d)R_e$— where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example, $R_d$ and $R_e$ may be joined together or with the N to form a 3- to 12-membered ring, e.g., morpholino or piperidinyl. The term amino also includes the corresponding quaternary ammonium salt of any amino group. Exemplary amino groups include alkyl amino groups, wherein at least one of $R_d$ and $R_e$ is an alkyl group.

The term "sulfonyl" as used herein refers to the structure $R_uSO_2$—, where $R_u$ can be alkyl, alkenyl, alkynyl, aryl, cycloalkyl, and heterocyclyl, e.g., alkylsulfonyl. The term "alkylsulfonyl" as used herein refers to an alkyl group attached to a sulfonyl group. "Alkylsulfonyl" groups can optionally contain alkenyl or alkynyl groups.

"Alkyl," "alkenyl," "alkynyl," and "amino" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and nitrogen. The substituents may be branched to form a substituted or unsubstituted heterocycle or cycloalkyl.

As used herein, a "suitable substituent" refers to a group that does not nullify the synthetic or enzymatic utility of the compounds of the invention or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO(($C_6$ aryl) esters, such as —$CO_2$($C_{1-22}$, $C_{1-8}$, and $C_{1-6}$ alkyl) and —$CO_2$ ($C_6$ aryl). One of skill in art can readily choose a suitable substituent based on the stability and pharmacological and synthetic activity of the compound of the invention.

The term "acceptable salt(s)" refers to salts of acidic or basic groups that may be present in compounds used in the present compositions. Acceptable salts include salts which will not interfere with the reactions contemplated by the invention and are not otherwise undesirable. Acceptable salts do not differ in activity from their free base, and may include salts commonly referred to as pharmaceutically acceptable salts, which are non-toxic salts that retain the biological activity of the free base. Compounds included in the present compositions that are acidic in nature are capable of forming base salts with various cations. Examples of such salts include alkali metal or alkaline earth metal salts, including, for example, calcium, magnesium, sodium, lithium, and potassium salts. Acceptable salts may also include zinc, iron, ammonium, copper, manganese, aluminum salts and the like. Acceptable salts may also be those derived from organic non-toxic bases, and may include salts of primary, secondary, and tertiary amines, substituted amines, including naturally occurring substituted amines, cyclic amines and basic ion exchange resins, such as isopropylamine, tripropylamine, ethanolamine, 2-diethylaminoethanol, 2-dimethyl amino ethanol, dicyclohexylamine, lysine, arginine, histidine, caffeine, procain, hydrabamine, choline, betaine, ethylenediamine, glucosamine, methylglucamine, theobromine, purines, piperazines, piperidine, polyamine resins and the like. In addition, salts may be formed from acid addition of certain organic and inorganic acids with basic centers of the purine, specifically guanine, or pyrimidine base. Finally it is to be understood that compounds of the present invention in their un-ionized as well as zwitterionic form and/or in the form of hydrates or solvates are also considered part of the present invention.

Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quenching group, its absorption spectrum must overlap the emission spectrum of the fluorophore. Efficient FRET interaction requires that the absorption and emission spectra of the pair have a large degree of overlap. The efficiency of FRET interaction is linearly proportional to that overlap. Typically, a large magnitude of signal (i.e., a high degree of overlap) is required. FRET pairs, including fluorophore-quenching group pairs, are therefore typically chosen on that basis.

The selection of appropriate FRET donor-acceptor pairs for particular probes may be referenced to the previous literature.

An exemplified synthesis method of nucleotide with an ester linkage between the 3'-end of sugar and a fluorescent dye is available in the FIG. 2 of the U.S. Pat. No. 5,798,210.

1.3 Utilizing 3' Modified Nucleotides by DNA Polymerases

Previous attempts were made to incorporate modified nucleotides containing bulky fluorescent dyes at the 3'-position with various DNA polymerases but none of them was satisfactory. Such failure may be attributed to the close proximity of the 3'-end position of deoxyribose and amino acid residues in the active sites of polymerases, as simulation performed with the crystal structure data of T7 DNA polymerase. Among different DNA polymerases and various modified nucleotides of interest, however, some polymerases seemed to have the space in the active site pockets to accommodate certain sizes of dyes or attachments at the 3'-end of tested nucleotides (Canard et al., 1995; Kim et al., 2010).

Therminator™ II DNA Polymerase is a 9° N™ DNA Polymerase variant (D141A/E143A/A485L/Y409V). This enzyme is derived from its predecessor, Therminator DNA Polymerase, and differs by having one additional amino acid change (Y409V) that allows the enzyme more efficient incorporation of ribonucleotides and nucleotides with modified 3' functional groups. Therminator II is capable of utilizing 3'-O-coumarin dTTPs, with an up to six-carbon linker between the ribose and its coumarin attachment, in the primer extension reactions.

A previous study has demonstrated that a group of 3'-modified nucleotides, including 3'-fluothioureido-dTTP, can be incorporated into DNA by DNA polymerases, such as Taq DNA polymerase, Sequenase 2.0 (United States Biochemicals, Cleveland, Ohio), and HIV-RT (Boehringer Mannheim). More intriguingly, as mentioned earlier, the latter two enzymes can hydrolyze the ester and amido bonds at the nascent 3' end of DNA to leave behind the hydroxyl and amine group, respectively. By comparison, Sequenase 2.0 can incorporate multiple 2'-deoxy-3'-anthranyloy-dNTPs consecutively to the end of a primer extension reaction but Taq DNA polymerase stops at only one nucleotide addition. Sequenase 2.0 is a genetically engineered mutant of T7 DNA polymerase by in vitro mutagenesis; it is different from its wild type by having virtually no 3' to 5' exonuclease activity. Therefore, this esterase-like catalytic editing activity of Sequenase 2.0 may not be relating to the 3' to 5' exonulease activity of T7 DNA polymerase. From the viewpoint of real time sequencing, the catalytic editing activities of some DNA polymerases can be of value to detach a base-specific fluorescent label at the 3'-end of each nucleotide, for example, through hydrolyzing ester bond, for a base reporting purpose when using fluoresce labeled nucleotides in sequencing. Every fluorescence-labeled nucleotide that involves in DNA primer extension, in a sequencing-by-synthesis approach, will come to the active site of DNA polymerase and present its fluorescent signal before the attached fluorescent label is cleaved off in the process of primer extension.

EXAMPLES

The sequencing methods described in the present invention are applied to sequence one or more DNA molecules. A solution of circular, single-stranded DNA molecules with an average length of 200 nt at a concentration of 0.1 molecules per attoliter in a suitable sequencing reaction buffer is applied to a detection apparatus as described in U.S. patent application entitled "Single-molecule Detection System and Methods," and in U.S. Pat. App. No. 61/314,037, filed Mar. 15, 2010. Alternatively, the solution of circular, single-stranded DNA molecules is applied to a detection apparatus as described in U.S. patent application Ser. No. 12/801,503, filed Jun. 11, 2010; U.S. patent application Ser. No. 12/805,411, filed Jul. 29, 2010 and U.S. Pat. Nos. 6,917,726; 7,170,050.

The circular DNA molecules contain a known insert sequence of approximately 20 nucleotides 3' to an unknown sample sequence. A sequencing primer complementary to the known insert sequence and four types of fluorophore labeled nucleotide analogs according to the invention are provided. The four nucleotide analogs may comprise the complementary base B as adenine, cytosine, guanine, or thymidine. In a plurality of detection sites in the detection apparatus, a ternary complex of a DNA polymerase, DNA molecule(s), and sequencing primers is formed and the polymerase incorporates one fluorescently labeled nucleotide analog to the 3' end of the sequencing primer.

In the plurality of detection sites, a fluorescently labeled nucleotide analog, which associates with the active site of the polymerase and is incorporated into the growing (primer) strand, is excited by the excitation light from a light source coupled to the detection apparatus and then emits fluorescent light. This fluorescent light detected by the detection apparatus is output as signals to be processed, so as to identify the base comprised by the nucleotide analog added to the sequencing primer. The fluorescent light (signal) disappears when the polymerase cleaves off the 3'-end attachment, which comprises the fluorescent label from the growing strand, leaving the 3'-OH of the complementary group comprising the base B.

The cycle of incorporating the 3'-labeled nucleotide analog by the polymerase is repeated several times to acquire a sequencing reading at least three times the length of the DNA molecule (i.e., the DNA molecule is sequenced and re-sequenced twice). The sequence of the DNA molecule is then obtained computationally by accepting or rejecting sequencing repeats and determining a consensus sequence from an alignment of the accepted repeats, as described in U.S. Pat. Pub. No. 2010/0121582, published May 13, 2010.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Example 1

In this and the following examples, exemplary nucleotide analogs may comprise the bases B, and/or the linker(s) L, $L_m$ or $L_{m+1}$, the fluorophore F, the group Y, $R_m$ and $R_{m+1}$, each having an identity as described herein for nucleotide analogs having a structure of Formula I, supra.

Exemplary nucleotide triphosphate analogs have structure as shown in the following:

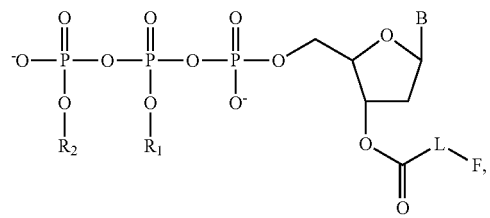

Formula III

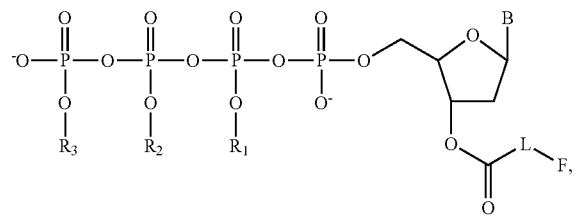

Formula IV

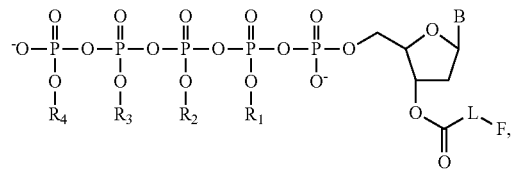

Formula V

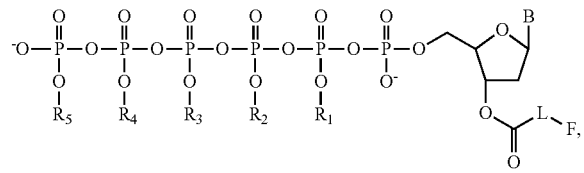

Formula VI

-continued

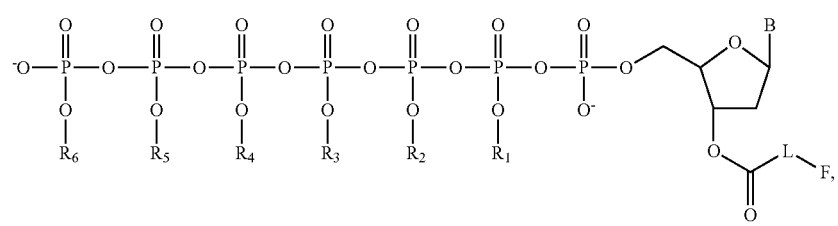
Formula VII

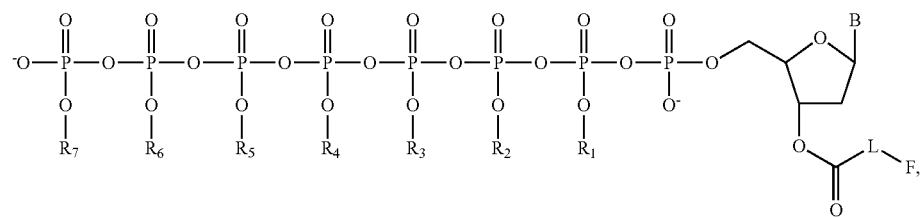
Formula VIII

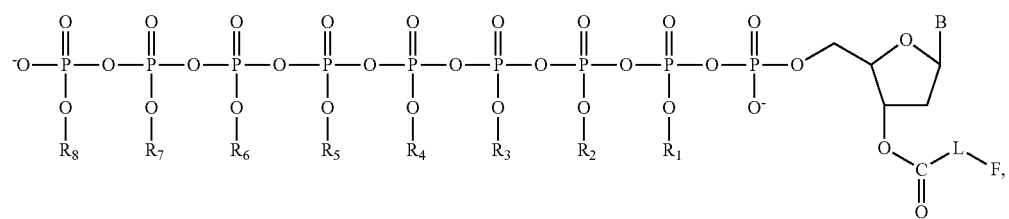
Formula IX

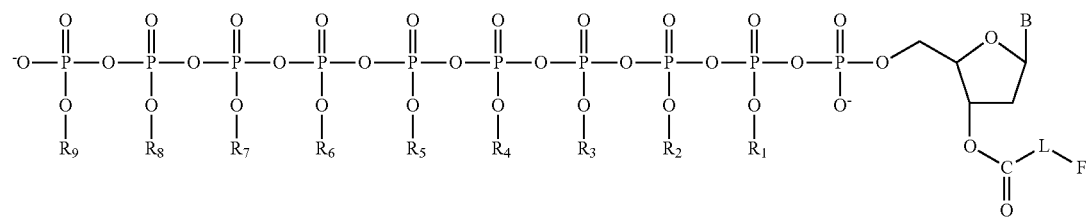
Formula X

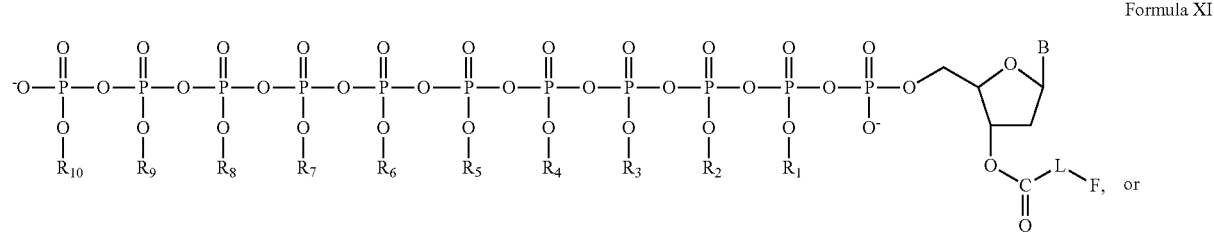
Formula XI, or

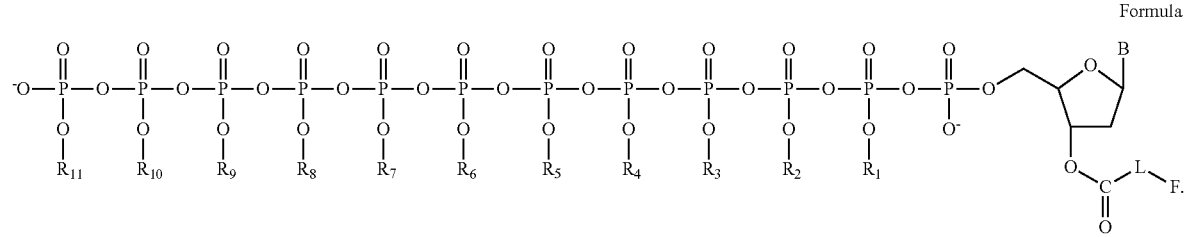
Formula XII.

wherein $R_1$, $R_2$, $R_3$, $R_4$, $R_5$, $R_6$, $R_7$, $R_8$, $R_9$, $R_{10}$ and $R_{11}$ each independently represents a hydrogen (H) or a functional group consisting of a linker group ($L_1$, $L_2$, $L_3$, $L_4$, $L_5$, $L_6$, $L_7$, $L_8$, $L_9$, $L_{10}$ and $L_{11}$ respectively corresponding to $R_1$, $R_2$, $R_3$, $R_4$, $R_5$, $R_6$, $R_7$, $R_8$, $R_9$, $R_{10}$ and $R_{11}$) and a fluorescence quenching moiety $Q_1$, $Q_2$, $Q_3$, $Q_4$, $Q_5$, $Q_6$, $Q_7$, $Q_8$, $Q_9$, $Q_{10}$ and $Q_{11}$ respectively corresponding to $R_1$, $R_2$, $R_3$, $R_4$, $R_5$, $R_6$, $R_7$, $R_8$, $R_9$, $R_{10}$ and $R_{11}$);

F represents a photo-detectable label or a fluorescent dye;

B represents a base selected from adenine, cytosine, guanine, thymine, uracil, hypoxanthine, and 5-methylcytosine;

$L_1$, $L_2$, $L_3$, $L_4$, $L_5$, $L_6$, $L_7$, $L_8$, $L_9$, $L_{10}$ and $L_{11}$ are linkers, and each of which is selected from alkyl, alkenyl, alkynyl, aryl, heteroaryl, heterocyclyl, polyethylene glycol, ester, amino, sulfonyl, or a combination thereof; and $Q_1$, $Q_2$, $Q_3$, $Q_4$, $Q_5$, $Q_6$, $Q_7$, $Q_8$, $Q_9$, $Q_{10}$ and $Q_{11}$ are quenchers, and each of which is independently chosen from those compounds that can decrease the signal from the photo-detectable label or fluorescence dye (F) used in the same molecule.

A schematic illustration (FIG. 1) of a single cycle of proofreading-dependent sequencing by synthesis using a modified dinucleotide analog is provided in an US Pat. Publication No. 20110300534. The reaction complex comprising a proofreading polymerase, a target (template) strand, and a replicating strand are exposed to the excitation light. An incoming dinucleotide analog having adenine as the first base associates with the active site of the polymerase and base pairs with a thymine base in the target strand. The dinucleotide analog is incorporated into the growing strand by the polymerase, whereupon the fluorescent label F is excited by the excitation light and emits a signal captured by a detector. As shown in the spectrogram, this signal remains detectable until the unpaired moiety of the analog (comprising the second base X which is not able to base pair with the subsequent base in the target strand and the fluorescent label F at its 3'-end) is cleaved from the growing strand by the exonuclease activity of the polymerase. The signal disappears as the labeled, unpaired moiety of the analog dissociates from the reaction complex. This case is quite similar to what we propose in this disclosure. Instead of using the exonuclease activity of the DNA polymerase, an esterase activity of some DNA polymerases is involved in this example.

A modified nucleotide has the structure of Formula XIII is replacing the dinucleotide analog in the reaction described above. The fluorescent signal is on once the modified nucleotide associates with the active site of the polymerase and its adenine moiety base pairs with a thymine base in the target strand. The nucleotide analog is incorporated into the growing strand by the polymerase, and this signal continues being detectable until the fluorophore gets cleaved off from the nascent strand by the enzyme at the ester linkage. The nucleotide added in this primer extension event can be identified by the kind of fluorescent probe attached on the modified nucleotide.

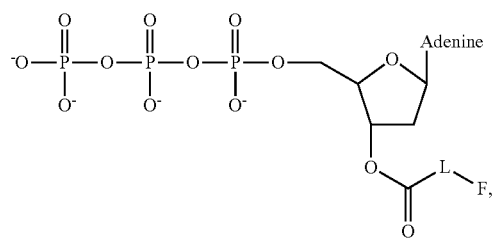

Formula XIII wherein F represents a fluorescent dye; and
L represents a linker that is selected from alkyl, alkenyl, alkynyl, aryl, heteroaryl, heterocyclyl, polyethylene glycol, ester, amino, sulfonyl, or a combination thereof

Example 2

An exemplary triphosphate analog comprising a fluorescence quenching moiety Q has a structure of Formula XI:

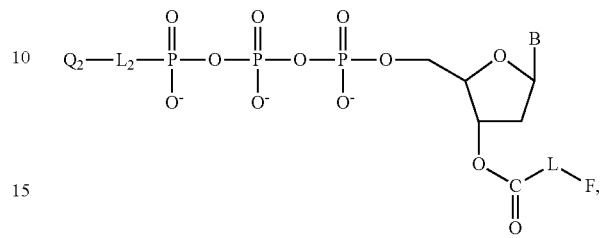

Formula XIV wherein $Q_2$ is a fluorescence quencher;
B represents a base selected from adenine, cytosine, guanine, thymine, uracil, hypoxanthine, or 5-methylcytosine;
F represents a fluorescent dye; and
L and $L_2$ are linkers, and each is independently selected from alkyl, alkenyl, alkynyl, aryl, heteroaryl, heterocyclyl, polyethylene glycol, ester, amino, sulfonyl, or a combination thereof.

The additional quencher (Q) is added to lower the general background due the appearances of those fluorescent dyes attached to the modified nucleotides when they show up in the signal-detectable volume in the reaction space.

Example 3

An exemplary triphosphate analog with a phosphorothioate in place of the alpha-phosphate of the triphosphate chain, thereby preventing processive 3' to 5' exonuclease activity possessed by some of the polymerase, has a structure as shown in Formula XV:

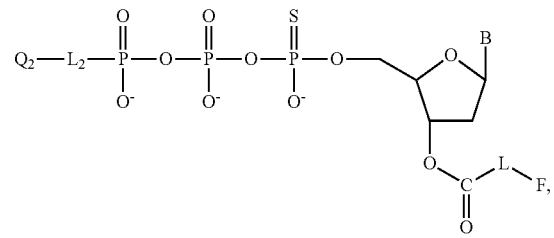

Formula XV wherein $Q_2$ is a fluorescence quencher;
B represents a base selected from adenine, cytosine, guanine, thymine, uracil, hypoxanthine, or 5-methylcytosine;
F represents a fluorescent dye; and
L and $L_2$ are linkers, and each is independently selected from alkyl, alkenyl, alkynyl, aryl, heteroaryl, heterocyclyl, polyethylene glycol, ester, amino, sulfonyl, or a combination thereof.

A further consideration of some common DNA polymerases may also possess 3' to 5' exonuclease activities, the sulfur replacement at the alpha-phosphate of the modified nucleotide can be used to skew the reaction to have a lower chance of having a chew in (3' to 5') from the newly added nucleotide as to result in getting wrong sequencing outcomes.

The invention claimed is:

1. A method of using nucleotide analogs to determine a nucleotide sequence of a target nucleic acid, comprising the steps of:
    (a) providing a reaction complex comprising a target nucleic acid, a primer nucleic acid comprising a sequence which is complementary to a region of the target nucleic acid, and a nucleic acid-polymerizing enzyme, enzyme complex, or enzyme mixture that possesses a 5' to 3' polymerization activity and a 3' catalytic editing activity;
    (b) contacting the reaction complex with nucleotide analogs, wherein each nucleotide analog comprises a base moiety and at least one label moiety comprising a photo-detectable label, wherein the photo-detectable label is connected to a 3' position of a sugar of the nucleotide analog via a coupler group, and the at least one label moiety includes a linker group selected from alkyl, alkenyl, alkynyl, aryl, heteroaryl, heterocyclyl, polyethylene glycol, ester, sulfonyl or a combination thereof, connecting the photo-detectable label to the coupler group, and the nucleotide analog has a structure as shown in Formula I or Formula II:

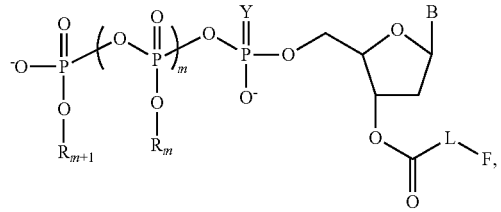

Formula I

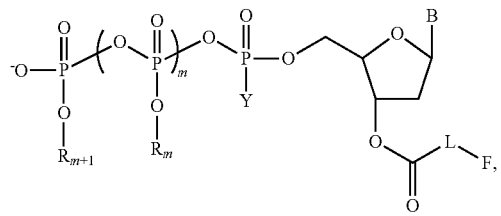

Formula II wherein m is an integer and 1≤m≤10, L represents the linker group;

$R_m$ and $R_{m+1}$ vary as m varies, and when m is larger than 1, $R_m$ refers to a set of functional groups ranging from $R_1$ to $R_m$, each of $R_m$ may represent independently hydrogen (H) or a functional group consisting of a linker group $L_m$ and a quencher $Q_m$, while $R_{m+1}$ may represent hydrogen (H) or a functional group consisting of a linker group $L_{m+1}$ and the quencher $Q_{m+1}$, the quencher $Q_m$ or $Q_{m+1}$ is independently chosen and applied to decrease the fluorescent signal generated from the fluorescent dye at the 3'-end of the nucleotide; the linker group $L_m$ or $L_{m+1}$ is independently selected from alkyl, alkenyl, alkynyl, aryl, heteroaryl, heterocyclyl, polyethylene glycol, ester, amino, sulfonyl, or a combination thereof;

F represents a photo-detectable label;

B represents a base selected from adenine, cytosine, guanine, thymine, uracil, hypoxanthine or 5-methylcytosine; and Y in Formula I represents oxygen (O) or sulfur (S), while Y in Formula II represents methyl (—CH$_3$) or boryl (—BH$_2$);

(c) allowing the nucleic acid-polymerizing enzyme, enzyme complex, or enzyme mixture to incorporate one nucleotide analog to the primer nucleic acid to form a nascent primer strand via the 5' to 3' polymerization activity of the nucleic acid-polymerizing enzyme, enzyme complex, or enzyme mixture, whereby the at least one label moiety and the base moiety of the nucleotide analog are incorporated in the nascent primer strand;
    (d) detecting the photo-detectable label of the at least one label moiety and determining an identity of the base moiety of the incorporated nucleotide analog;
    (e) removing the at least one label moiety of the incorporated nucleotide analog from the nascent primer strand via the 3' catalytic editing activity of the nucleic acid-polymerizing enzyme, enzyme complex, or enzyme mixture; and
    (f) repeating steps (c)-(e) to determine the nucleotide sequence of the target nucleic acid.

2. A method of using nucleotide analogs to determine a nucleotide sequence of a target nucleic acid, comprising the steps of:
    (a) providing a reaction complex comprising a target nucleic acid, a primer nucleic acid comprising a sequence which is complementary to a region of the target nucleic acid, and a nucleic acid-polymerizing enzyme, enzyme complex, or enzyme mixture that possesses a 5' to 3' polymerization activity and a 3' catalytic editing activity;
    (b) contacting the reaction complex with nucleotide analogs, wherein each nucleotide analog comprises a base moiety and at least one label moiety comprising a photo-detectable label, wherein the photo-detectable label is connected to a 3' position of a sugar of the nucleotide analog via a coupler group, and the at least one label moiety includes a linker group selected from alkyl, alkenyl, alkynyl, aryl, heteroaryl, heterocyclyl, polyethylene glycol, ester, sulfonyl or a combination thereof, connecting the photo-detectable label to the coupler group, and the nucleotide analog has a structure as shown in Formula XVI:

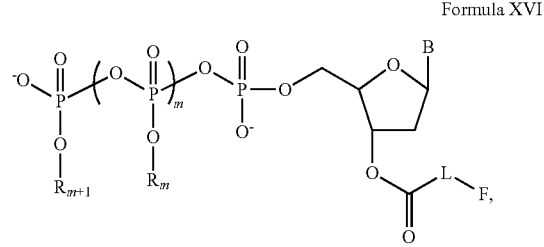

Formula XVI wherein m is an integer and 1≤m≤10, L represents the linker group;

$R_m$ and $R_{m+1}$ vary as m varies, and when m is larger than 1, $R_m$ refers to a set of functional groups ranging from $R_1$ to $R_m$, each of $R_m$ may represent independently hydrogen (H) or a functional group consisting of a linker group $L_m$ and a quencher $Q_m$, while $R_{m+1}$ may represent hydrogen (H) or a functional group consisting of a linker group $L_{m+1}$ and the quencher $Q_{m+1}$, the quencher $Q_m$ or $Q_{m+1}$ is independently chosen and applied to decrease the fluorescent signal generated from the fluorescent dye at the 3'-end of the nucleotide; the linker group $L_m$ or $L_{m+1}$ is independently selected from alkyl, alkenyl, alkynyl, aryl, heteroaryl, heterocyclyl, polyethylene glycol, ester, amino, sulfonyl, or a combination thereof;

F represents a photo-detectable label; and

B represents a base selected from adenine, cytosine, guanine, thymine, uracil, hypoxanthine or 5-methylcytosine;

(c) allowing the nucleic acid-polymerizing enzyme, enzyme complex, or enzyme mixture to incorporate one nucleotide analog to the primer nucleic acid to form a nascent primer strand via the 5' to 3' polymerization activity of the nucleic acid-polymerizing enzyme, enzyme complex, or enzyme mixture, whereby the at least one label moiety and the base moiety of the nucleotide analog are incorporated in the nascent primer strand;

(d) detecting the photo-detectable label of the at least one label moiety and determining an identity of the base moiety of the incorporated nucleotide analog;

(e) removing the at least one label moiety of the incorporated nucleotide analog from the nascent primer strand via the 3' catalytic editing activity of the nucleic acid-polymerizing enzyme, enzyme complex, or enzyme mixture; and (f) repeating steps (c)-(e) to determine the nucleotide sequence of the target nucleic acid.

3. A method of using nucleotide analogs to determine a nucleotide sequence of a target nucleic acid, comprising the steps of:

(a) providing a reaction complex comprising a target nucleic acid, a primer nucleic acid comprising a sequence which is complementary to a region of the target nucleic acid, and a nucleic acid-polymerizing enzyme, enzyme complex, or enzyme mixture that possesses a 5' to 3' polymerization activity and a 3' catalytic editing activity;

(b) contacting the reaction complex with nucleotide analogs, wherein each nucleotide analog comprises a base moiety and at least one label moiety comprising a photo-detectable label, wherein the photo-detectable label is connected to a 3' position of a sugar of the nucleotide analog via a coupler group, and the at least one label moiety includes a linker group selected from alkyl, alkenyl, alkynyl, aryl, heteroaryl, heterocyclyl, polyethylene glycol, ester, sulfonyl or a combination thereof, connecting the photo-detectable label to the coupler group, and the nucleotide analog has a structure as shown in Formula IA or Formula IIA:

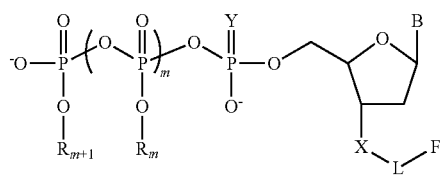

Formula IA

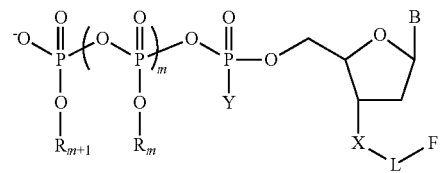

Formula IIA wherein m is an integer and $1 \le m \le 10$, L represents the linker group;

$R_m$ and $R_{m+1}$ vary as m varies, and when m is larger than 1, $R_m$ refers to a set of functional groups ranging from $R_1$ to $R_m$, each of $R_m$ may represent independently hydrogen (H) or a functional group consisting of a linker group $L_m$ and a quencher $Q_m$, while $R_{m+1}$ may represent hydrogen (H) or a functional group consisting of a linker group $L_{m+1}$ and the quencher $Q_{m+1}$, the quencher $Q_m$ or $Q_{m+1}$ is independently chosen and applied to decrease the fluorescent signal generated from the fluorescent dye at the 3'-end of the nucleotide; the linker group $L_m$ or $L_{m+1}$ is independently selected from alkyl, alkenyl, alkynyl, aryl, heteroaryl, heterocyclyl, polyethylene glycol, ester, amino, sulfonyl, or a combination thereof;

X represents the coupler group selected from —O—, —S—, —HN—, —COO—, —CO—, —NH(CS)NH—, or —NHCO—;

F represents a photo-detectable label;

B represents a base selected from adenine, cytosine, guanine, thymine, uracil, hypoxanthine or 5-methylcytosine; and Y in Formula I represents oxygen (O) or sulfur (S), while Y in Formula II represents methyl (—CH$_3$) or boryl (—BH$_2$);

(c) allowing the nucleic acid-polymerizing enzyme, enzyme complex, or enzyme mixture to incorporate one nucleotide analog to the primer nucleic acid to form a nascent primer strand via the 5' to 3' polymerization activity of the nucleic acid-polymerizing enzyme, enzyme complex, or enzyme mixture, whereby the at least one label moiety and the base moiety of the nucleotide analog are incorporated in the nascent primer strand;

(d) detecting the photo-detectable label of the at least one label moiety and determining an identity of the base moiety of the incorporated nucleotide analog;

(e) removing the at least one label moiety of the incorporated nucleotide analog from the nascent primer strand via the 3' catalytic editing activity of the nucleic acid-polymerizing enzyme, enzyme complex, or enzyme mixture; and (f) repeating steps (c)-(e) to determine the nucleotide sequence of the target nucleic acid.

4. The method of claim 1, wherein the photo-detectable label is a fluorophore or a fluorescent dye.

5. The method of claim 2, wherein the nucleotide analog has 3-12 phosphate groups at the 5'-end of the nucleotide analog.

6. The method of claim 3, wherein the nucleotide analog has 3-12 phosphate groups at the 5'-end of the nucleotide analog.

7. The method of claim 1, wherein the nucleotide analog has 3-12 phosphate groups at the 5'-end of the nucleotide analog.

8. The method of claim 2, wherein the photo-detectable label is a fluorophore or a fluorescent dye.

9. The method of claim 3, wherein the photo-detectable label is a fluorophore or a fluorescent dye.

* * * * *